(12) United States Patent
Danehorn et al.

(10) Patent No.: US 7,641,615 B2
(45) Date of Patent: Jan. 5, 2010

(54) METHOD AND DEVICE FOR REMOVING OSCILLATORY ARTEFACTS FROM INVASIVE BLOOD PRESSURE MEASUREMENT DATA

(75) Inventors: Kenneth Danehorn, Vaxholm (SE); Fredrik Gustafsson, Linköping (SE); Johan Wallin, Linköping (SE)

(73) Assignee: Siemens Aktiengesellschaft, Munich (DE)

( * ) Notice: Subject to any disclaimer, the term of this patent is extended or adjusted under 35 U.S.C. 154(b) by 325 days.

(21) Appl. No.: 11/541,264

(22) Filed: Sep. 29, 2006

(65) Prior Publication Data
US 2007/0124127 A1 May 31, 2007

(30) Foreign Application Priority Data
Sep. 29, 2005 (EP) .................... 05021338

(51) Int. Cl.
*A61B 5/02* (2006.01)
(52) U.S. Cl. ........................... 600/486
(58) Field of Classification Search ............. 600/486
See application file for complete search history.

(56) References Cited

U.S. PATENT DOCUMENTS
6,290,652 B1 * 9/2001 Wellnhofer .................. 600/486

OTHER PUBLICATIONS

Hamparsum Bozdogan, "Statistical Data Mining and Knowledge Discovery", CRC Press, 2004, p. 144-145.*
Johan Wallin, "Catheter-Compensated Pressure Measurement", Mar. 30, 2005, pp. i-viii, pp. 1-45.

* cited by examiner

*Primary Examiner*—Charles A Marmor, II
*Assistant Examiner*—Christian Y Jang

(57) ABSTRACT

The invention relates to a method for removing oscillatory artefacts caused by pressure waves in a fluid-filled transluminal catheter from invasive blood pressure measurement data, including the steps of setting up a model for the measurement data, fitting the model to the measurement data, identifying the model components, representing the oscillatory artefact, and removing the oscillatory artefact from the measurement data. The invention also relates to a respective device for acquiring and correcting invasive blood pressure measurement data.

7 Claims, 3 Drawing Sheets

METHOD AND DEVICE FOR REMOVING OSCILLATORY ARTEFACTS FROM INVASIVE BLOOD PRESSURE MEASUREMENT DATA

CROSS REFERENCE TO RELATED APPLICATIONS

This application claims priority of European application No. EP05021338.8 filed Sep. 29, 2005, which is incorporated by reference herein in its entirety.

FIELD OF THE INVENTION

The present invention relates to a method and device for removing oscillatory artefacts caused by pressure waves in a fluid-filled trans-luminal catheter from invasive blood pressure measurement data.

BACKGROUND OF THE INVENTION

In the diagnosis of cardiovascular diseases, cardiac catheterization can be a valuable tool for the cardiologist. During this procedure, the blood pressure is invasively measured by inserting a catheter into the patient's heart or a major artery. The pressure variations are transferred through the fluid-filled catheter to a pressure sensor placed on a table beside the patient. The blood pressure waveform may be measured over several heartbeats, and diagnostic parameters such as maximum systolic pressure (SP), beginning of diastolic pressure (BDP), and end diastolic pressure (EDP) may be derived from the blood pressure waveform.

However, the measured blood pressure data include artefacts caused by oscillatory pressure waves in the fluid column in the catheter. This phenomenon is illustrated in FIG. 1, where the true blood pressure wave form over one heartbeat is denoted 1 and the measured blood pressure is denoted 2. It can be seen that the true blood pressure 1 is superimposed with a higher frequency oscillation. Such oscillations negatively affect the diagnostic value of the measurement.

SUMMARY OF THE INVENTION

Therefore, it is an object of the present invention to provide a method for removing oscillatory artefacts caused by pressure waves in a catheter from invasive blood pressure measurement data, as well as a device for acquiring and correcting such invasive blood pressure measurement data.

The invention achieves these objects by the method and the device according to the dependent claims. Preferred embodiments of the invention are defined in the respective dependent claims.

According to the claims, the method of the invention includes the following steps: setting up a model for the measurement data, fitting the model to the measurement data, identifying a model component representing the oscillatory artefact, and removing the oscillatory artefact from the measurement data. Thereby, it is possible to estimate the invasive blood pressure at the tip of the catheter, i.e. in the patient's heart or blood vessel, based on measurements made through a fluid-filled catheter. For example by modelling the transfer function of the catheter, the pressure at the tip of the catheter can be estimated by fitting the model to the measurement data, for example by an adaptive compensation.

According to a preferred embodiment, the damping coefficient and the natural frequency of the oscillatory artefact are estimated and used to identify the model component representing the oscillatory artefact. Preferably, the damping coefficient and the natural frequency of the oscillatory artefact are estimated from measuring a step response of the catheter.

According to a further preferred embodiment, the model is a high-order auto-regression model that generates the measurement data when fed with white noise. Such model is preferably fitted to the measurement data in the Z-transformed domain. The Z-transform is similar to the Fourier-transform, but applies to discrete data, such as the measured blood pressure data. The Z-transform of a sequence of data points x(n) is defined as $$X(z) = \sum_{n=-\infty}^{\infty} x(n)z^{-n} \tag{1}$$

In the Z-transformed domain, both the measurement data and the chosen model will have several poles. The poles in the Z-plane are indicative of the frequency response of the system; they particularly indicate where the gain of the filter transfer function will be infinite. Based on the position of the poles and zeros, one can quickly determine the frequency response of a system. This is a result of the correspondence between the frequency response and the transfer function evaluated on the unit circle in the pole/zero plot.

Preferably, the catheter poles originating from the oscillatory artefacts are identified in the Z-transform of the model, separated from the heart-related poles, and used to remove the oscillatory artefact from the measurement data. This may be done by deriving values for the damping coefficient and the natural frequency of the oscillatory artefact from the position of the catheter poles, and using these values to inverse filter the measurement data. Thereby, a good estimate of the true blood pressure wave form may be obtained. Alternatively, the catheter poles may be removed from the fitted model by other means.

In a preferred embodiment, the estimated damping coefficient and natural frequency of the oscillatory artefact are used to calculate a first approximation of the position of the catheter poles in the Z-transformed domain.

The invention is also directed to a device for acquiring and correcting invasive blood pressure measurement data, including a fluid-filled catheter insertable into the heart or an artery of a patient, a sensor connectable to the catheter for measuring blood pressure, and a data processing module for removing oscillatory artefacts. The data processing module is adapted to setting up a model for the measurement data, fitting the model to the measurement data, identifying a model component representing the oscillatory artefact, and removing the oscillatory artefact from the measurement data. Preferably, the data processing module is adapted to carry out some or all of the above-described features.

BRIEF DESCRIPTION OF THE DRAWINGS

Preferred embodiments of the invention shall now be described with reference to the accompanying drawings, in which.

DETAILED DESCRIPTION OF THE INVENTION

Figure 1:
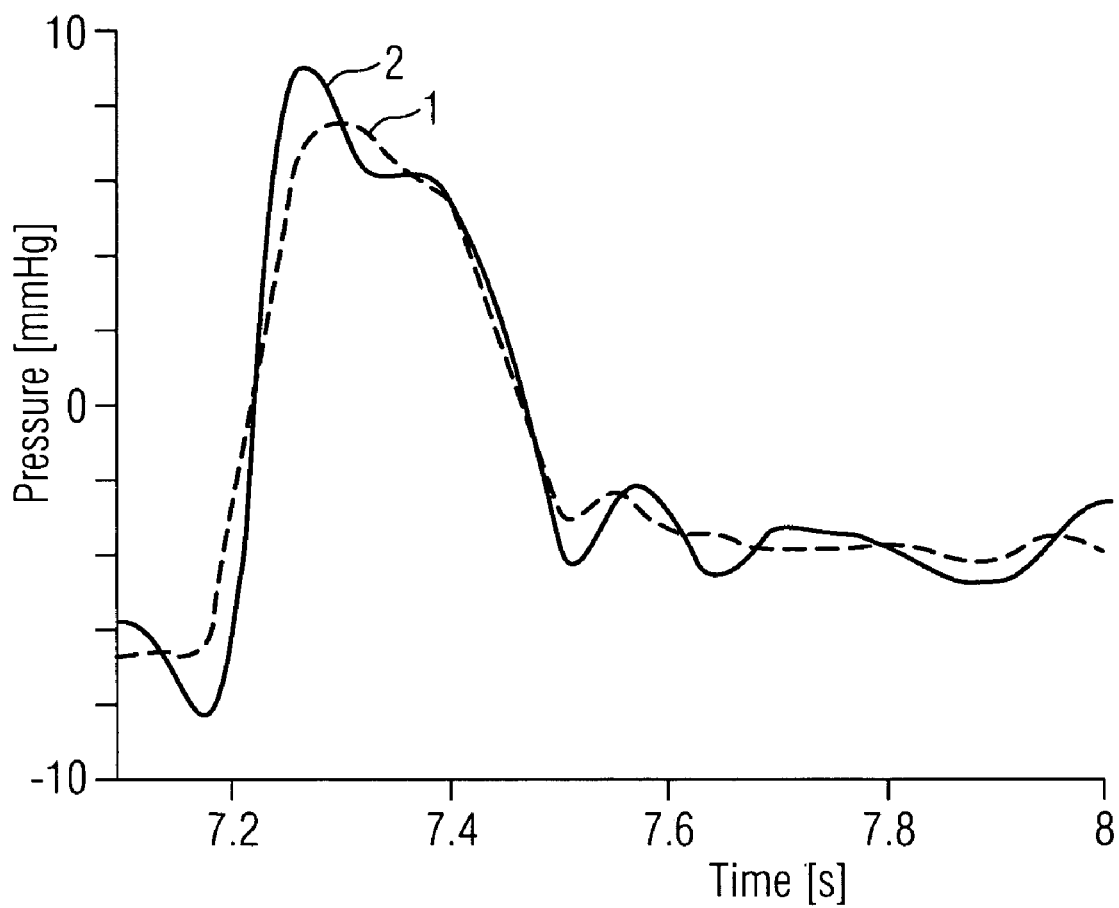
FIG. 1 shows a graph of measured and true blood pressure over time.
Figure 2:
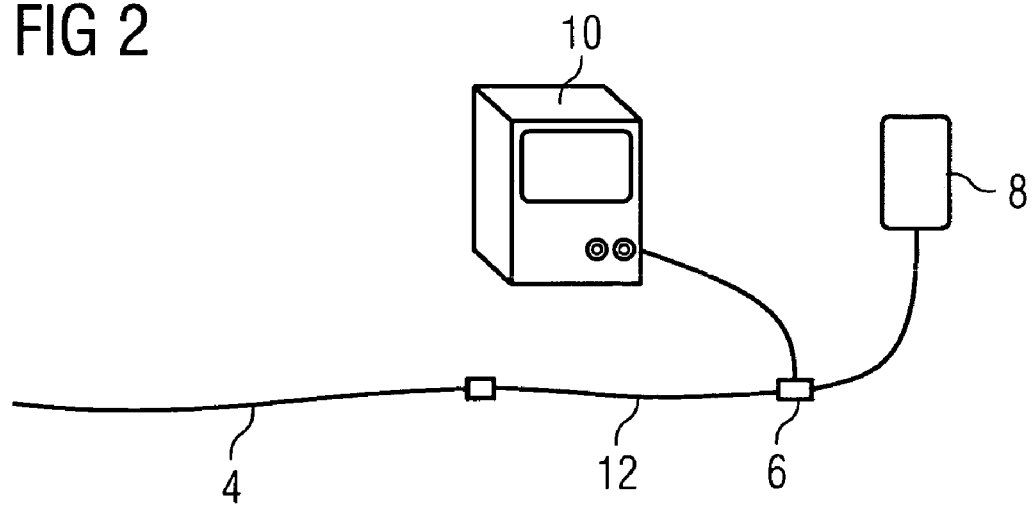
FIG. 2 is a schematic representation of a device for carrying out invasive blood pressure measurements.

The basic concepts of modelling a fluid-filled catheter shall first be explained with reference to FIG. 2. The recording device according to FIG. 2 has a catheter 4, which is connected via an extension tube 12 with the pressure sensor 6. The acquired data may be processed and viewed by means of data processing module 10. A saline solution 8 can be flushed through the system to keep it clear from air-bubbles and blood clotting. Such measuring device is commercially available e.g. from Becton Dickenson Critical Care systems.

The fluid column in catheter 4 transfers vibrations caused by pressure pulses in the heart to the sensor 6. The dynamics of the oscillations in the catheter are very similar to a mass-spring system. In particular, the system has a natural frequency $f_0$ at which it will oscillate when left alone. Further, friction will result in damping which may be indicated by a damping coefficient $\zeta$. In the case of a fluid-filled catheter, these parameters will depend on the viscosity of the fluid as well as the dimensions of the catheter tube.

By modelling the catheter as a tube with length 1, radius r and filled with a fluid with a viscosity $\eta$, which depends on the temperature of the blood inside the catheter, and by finding values for the hydraulic resistance $R_h$, the hydraulic inertance $L_h$ and the hydraulic compliance $C_h$ (equivalent to electric resistance, inductance and capacitance), a second order differential equation may be derived between the true blood pressure $P_u$ and the measured blood pressure $P_y$:

$$P_u \omega_0^2 = \frac{d^2 P_y}{dt^2} + 2\zeta\omega_0 \frac{dP_y}{dt} + \omega_0^2 P_y \qquad (2)$$

where $$f_0 = \frac{1}{2\pi\sqrt{L_h C_h}} = \frac{1}{2\pi}\sqrt{\frac{\pi r^2}{\rho l C_h}} \qquad (3)$$

and $$\zeta = \frac{R_h}{2}\sqrt{\frac{C_h}{L_h}} = \frac{4\eta}{r^3}\sqrt{\frac{lC_h}{\rho\pi}} \qquad (4)$$

The hydraulic resistance $R_h$, inertance $L_h$ and compliance $C_h$ may be expressed in the terms of the dimensions of the catheter 1, r and the viscosity $\eta$ as follows;

$$R_h = \frac{8\eta l}{\pi r^4}, \qquad (5)$$

$$L_h = \frac{\rho l}{\pi r^2}, \qquad (6)$$

and $$C_h = \frac{\Delta V}{\Delta P}, \qquad (7)$$

where $\Delta V$ is the volume of fluid that enters the catheter tube upon application of a pressure change $\Delta P$.

Thus, first estimates of the natural frequency $f_0$ and damping coefficient $\zeta$ may be calculated by using the basic dimension of the catheter.

As described below, these estimates may be used to find a first approximation of the catheter poles in the Z-transform of a high-order filter.

Figure 3:
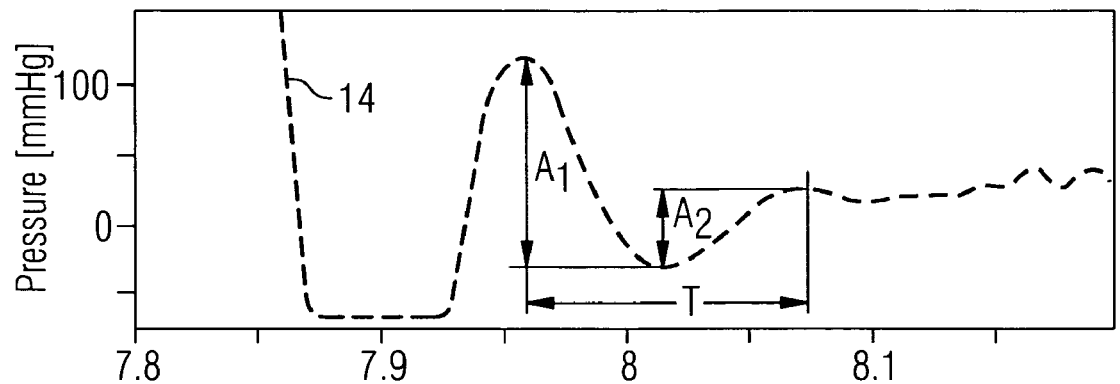
FIG. 3 is a graph of measured blood pressure versus time after a step response.

Alternatively, estimates for $f_0$ and $\zeta$ may be obtained from the step response of the catheter. This embodiment of the invention has the advantage that no assumptions have to be made on the catheter dimensions and the viscosity of blood inside the catheter. Instead, the catheter is flushed in vivo with saline. The measured blood pressure at the trailing edge of the pressure step is represented in FIG. 3. As is evident from FIG. 3, the blood pressure performs several oscillations with a periodic time T and amplitudes $A_1$ and $A_2$. By inserting these values into a model for a damped oscillatory system, the natural frequency and the relative damping coefficient may be derived as:

$$f_0 = \frac{\frac{1}{T}}{\sqrt{1-\zeta^2}} \qquad (8)$$

$$\zeta = \frac{\ln\left(\frac{A_1}{A_2}\right)}{\sqrt{\pi^2 + \ln\left(\frac{A_1}{A_2}\right)^2}} \qquad (9)$$

This method provides an easy way to estimate $f_0$ and $\zeta$.

Figure 4:
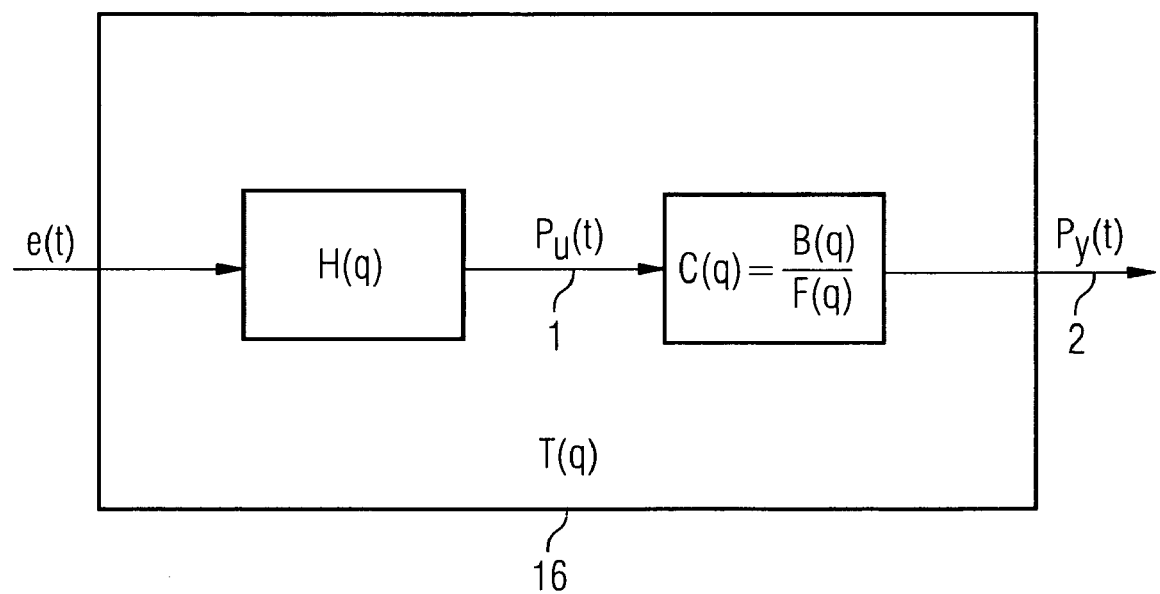
FIG. 4 is a schematic representation of the transfer function.
Figure 5:
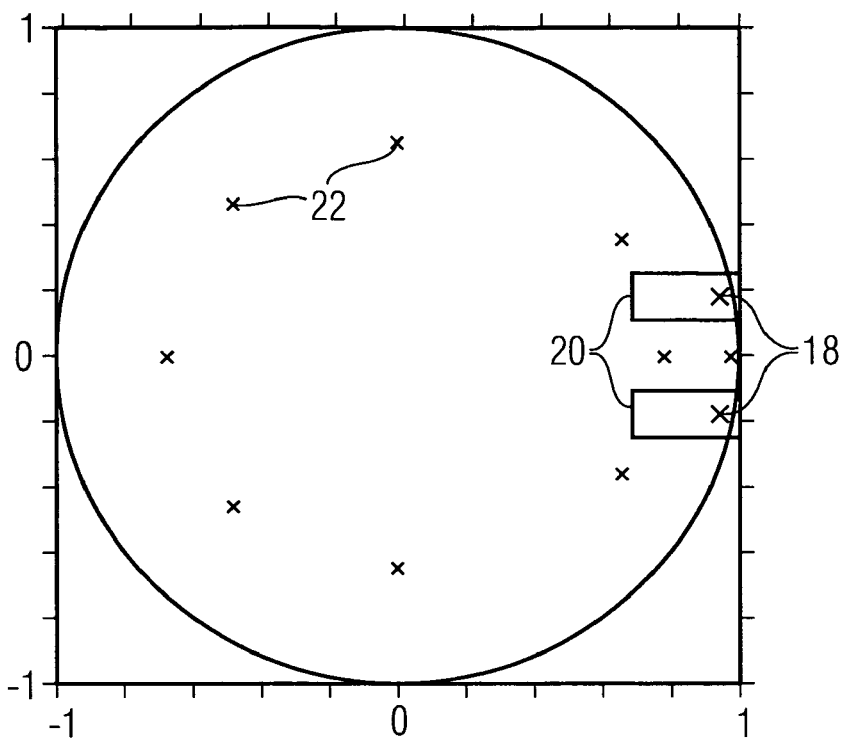
FIG. 5 is a representation of the Z-plane showing the poles of the fitted model after 0.4 seconds computation time.
Figure 6:
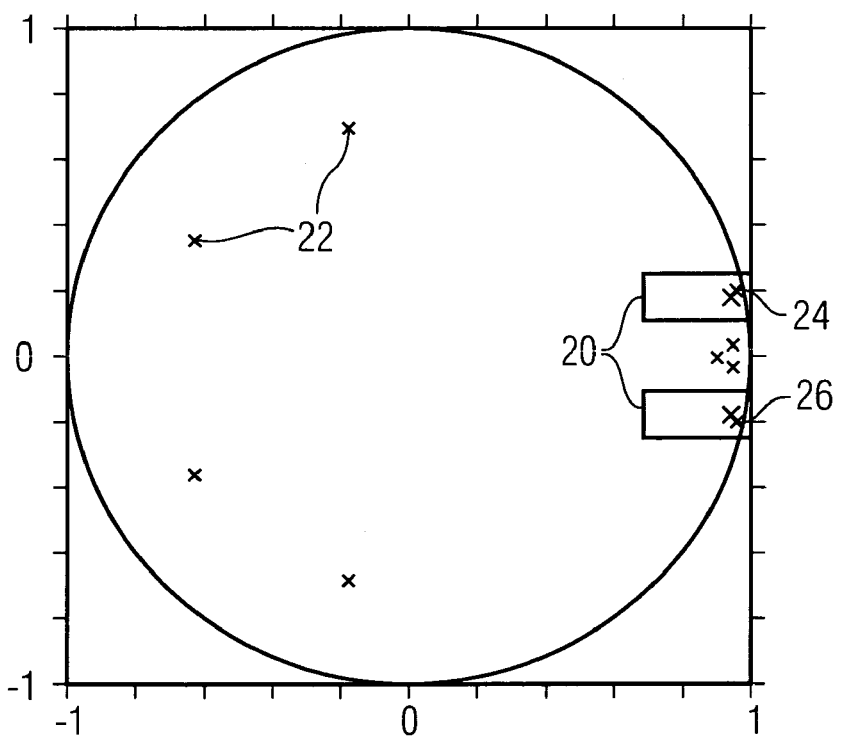
FIG. 6 is a representation of the Z-plane showing the poles of the fitted model after 10 seconds of computation time.

With reference to FIG. 4 to 6, an embodiment of the actual modelling of the oscillatory artefacts shall now be described.

According to this embodiment, the measurement data as well as a model of the measurement data are transformed to the Z-domain. In the Z-domain, the influence of the catheter oscillations will appear as one or several poles in the complex plane. The basic idea is to identify and separate the catheter poles F(q) from the other heart-related poles H(q) in a high-order filter T(q) and use those poles for compensation. The problem as illustrated in FIG. 4 is to find a filter 16, or T(q), which is the discrete transfer function (Z-transform) that generates the measured pressure waveform $P_y$ when fed with a stochastic signal such as white noise e(t). White noise may be used because it contains all frequencies and therefore maximally excites the system throughout all frequency components.

In the transfer function T(q), the catheter dynamics are included as C(q). C(q) may be described as a quotient of the polynomials B(q) and F(q). Since in this case the transfer function (Z-transform) of the catheter is a second order model (see equation (2)), B(q) can be approximated by a constant. F(q) however, includes the poles of the catheter transfer function.

According to an especially preferred embodiment, T(q) can be written as an auto-regression (AR) model. An auto-regression model is a model that regresses on the passed values of itself. If T(q) is chosen to be a $9^{th}$ order auto-regression model, it may be written as follows:

$$P_y(t) + a_1 P_y(t-1) + \ldots + a_9 P_y(t-9) = e(t), \qquad (10)$$

a relation of many delayed input signals, where $$\vartheta = (a_1 a_2 \ldots a_9)^T \qquad (11)$$

is the parameter vector of (in this case) 9 unknown parameters that needs to be adapted to the measured data. The order of the model is determined by the number of delayed input signals that are considered. A $9^{th}$ order model has proven to give good results, however, any order from 4 to 14 may also be considered. Preferably the order is 7 to 11, most preferred 8, 9 or 10.

By a recursive algorithm, the parameter vector θ is then adapted to the measured data such that the sum of squared prediction errors is minimized. Any recursive estimation method may be used, for example a least mean square algorithm or a recursive least square algorithm. The effect of such iterative estimation is shown in FIGS. 5 and 6, showing a representation of T(q) in the Z-plane after 0.4 seconds in FIG. 5 and after 10 seconds of computation in FIG. 6. In FIG. 5, 9 poles 22 of T(q) are distributed over the complex plane. From the estimated values of $f_0$ and the damping coefficient ζ, as explained above, estimates for the position of the catheter poles 18 have been previously calculated and are represented in FIGS. 5 and 6 by larger crosses 18. These poles are surrounded by rectangular areas 20, which represent the region in which a pole 22 of T(q) would be identified as a catheter pole. In FIG. 5, none of the 9 poles 22 are within the rectangular areas 20.

However, after 10 seconds of computation time, the auto-regressive model has been so far adapted that 2 poles 24 and 26 have moved inside the rectangular areas 20 and are situated very close to the estimated positions 18. Thus, these poles 24, 26 may be identified as originating from an influence of the fluid-filled catheter.

When the poles of F(q) have been identified in T(q), better estimates of the true values for the natural frequency $f_0$ and the damping coefficient ζ may be obtained from the position of the poles. By rewriting equation (2) as a difference equation, solving for $P_u$ and inserting the values for $f_0$ and ζ, the desired pressure $P_u(t)$ can be derived by inverse filtering as follow:

$$P_u = \left(1 + \frac{2\varsigma}{T\omega_0}\right)P_y(t) - \frac{2}{(T\omega_0)^2}(1 + \varsigma\omega_0 T)P_y(t-T) + \frac{1}{(T\omega_0)^2}P_y(t-2T) \quad (12)$$

where T is the periodic time or sampling period.

However, other know inverse filtering techniques using the numerator and denominator of the transfer function T(q) may be used as well, such as the filter function in Matlab.

We claim:

1. A method for removing an oscillatory artefact caused by a pressure wave in a fluid-filled trans-luminal catheter from an invasive blood pressure measurement data of a patient, comprising:
   generating a model for the measurement data by a data processing module;
   transforming the measurement data and the model of the measurement data to a Z-transformed domain by the data processing module;
   fitting the model to the measurement data in the Z-transformed domain by the data processing module;
   identifying a model component representing the oscillatory artefact by the data processing module; and
   removing the oscillatory artefact from the measurement data by the data processing module,
   wherein the model is a high-order auto-regression model that generates the measurement data when provided with a white noise, and
   wherein the model is a $9^{th}$ order auto-regression model.

2. The method as claimed in claim 1, wherein a damping coefficient and a natural frequency of the oscillatory artefact are estimated.

3. The method as claimed in claim 2, wherein the damping coefficient and the natural frequency of the oscillatory artefact are estimated from a measured step response of the catheter.

4. The method as claimed in claim 2, wherein the model component representing the oscillatory artefact is identified based on the damping coefficient and the natural frequency of the oscillatory artefact.

5. The method as claimed in claim 1, wherein the measurement data comprises a series of points sampled at a predetermined sampling rate.

6. The method as claimed in claim 1, wherein a catheter pole originating from the oscillatory artefact is:
   identified in the Z-transformed domain of the model,
   separated from a heart-related pole, and
   used to remove the oscillatory artefact from the measurement data.

7. The method as claimed in claim 6, wherein a first approximation of a position of the catheter pole identified in the Z-transformed domain is calculated based on an estimated damping coefficient and natural frequency of the oscillatory artefact.

* * * * *

UNITED STATES PATENT AND TRADEMARK OFFICE
CERTIFICATE OF CORRECTION

PATENT NO.       : 7,641,615 B2  Page 1 of 1
APPLICATION NO. : 11/541264
DATED            : January 5, 2010
INVENTOR(S)      : Danehorn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 423 days.

Signed and Sealed this

Sixteenth Day of November, 2010

David J. Kappos
*Director of the United States Patent and Trademark Office*